United States Patent [19]

Grob et al.

[11] Patent Number: 4,987,080

[45] Date of Patent: Jan. 22, 1991

[54] METHOD FOR IN VITRO MATURATION OF OOCYTES

[76] Inventors: Howard S. Grob, 1 University Rd., Great Neck, N.Y. 11020; Frank Friedman, Box 138, Quogue, N.Y. 11959

[21] Appl. No.: 115,994

[22] Filed: Nov. 3, 1987

[51] Int. Cl.$^5$ .............................................. C12N 5/00
[52] U.S. Cl. ........................... 435/240.25; 435/240.1; 435/240.2; 435/240.3; 435/240.31; 435/240.21
[58] Field of Search ............. 435/240.1, 240.2, 240.25, 435/240.3, 240.31

[56] References Cited

U.S. PATENT DOCUMENTS 4,589,402  5/1986  Hodgen et al. ............... 128/1 R
4,725,579  2/1988  Jones et al. ................. 514/12

OTHER PUBLICATIONS

Grob, H. S., "Enzymatic Dissection of the Mammalian Ovary", Science, Oct. 2, 1964, vol. 146, No. 3640, pp. 73–74.
Grob, H. S., "Growth and Endrocrine Function of Isolated Ovarian Follicles Cultivated in Vivo," Biology of Reproduction, 1, 320–323 (1969).
Grob, H. S., "Monolayer Culture of Ovarian Follicular Elements Derived from Isolated Mouse Follicles," Biology of Reproduction, 5, 207–213 (1971).
Hogan et al., "Manipulating the Mouse Embryo", Cold Spring Harbor Lab., (1986), pp. 107, 108 & 258.
McGaughey, in "Methods in Mammalian Reproduction", ed Daniel, Academic Press, New York, (1978), pp. 1–19.
Motlik et al., Soviet J. Dev. Biol. 12:269–273 (1982).
Skoblina, Soviet J. Dev. Biol. 13:1–14 (1982).
Barnes, Cell 22:649–655 (1980).
Diamond et al., J. Clin. Endocrin. & Metabolism 61:990–992 (1985).
Waymouth, in "Methods for Prep. of Media, Supp. & Substrate for Serum-Free Animal Cell Cult.", Alan R. Liss, New York (1984) pp. 23, 32.
Bashor, in "Methods in Enzymology" vol. LVIII, eds Jakoby et al., Academic Press, New York (1979), pp. 119–123.
Freshney, "Culture of Animal Cells", Alan R. Liss, New York (1983), pp. 75, 168 and 245.

Primary Examiner—Charles F. Warren
Assistant Examiner—Jasemine C. Chambers
Attorney, Agent, or Firm—Woodcock Washburn Kurtz Mackiewicz & Norris

[57] ABSTRACT

A method is disclosed for the in vitro growth and development of cells obtained from the follicles of a mammal to reproductively competent oocytes. By incubating these cells, which comprise small and medium oocytes, in a series of specific hormone-supplemented tissue culture media as described herein, they can be induced to grow and develop into reproductively competent oocytes. After a further maturation step in which chromosome number reduction occurs, the oocytes are fertilizable.

20 Claims, No Drawings

METHOD FOR IN VITRO MATURATION OF OOCYTES

BACKGROUND OF THE INVENTION

This invention relates to a method for generating large numbers of fertilizable ova from the ovarian tissue of a mammal. More specifically, it relates to methods for the in vitro development and maturation of germ cells recovered from the ovarian tissue of a mammal into fertilizable oocytes. These oocytes may be fertilized in vitro to form embryos which can be implanted into surrogate mothers.

The two commonly employed methods for breeding animals are natural mating and artificial insemination. In addition, a small number of animals are bred by embryo transfer. In this technique, a female is impregnated either naturally or by artificial insemination and six to ten days thereafter her uterus is flushed and any viable embryos are recovered. The recovered embryos are then implanted into surrogate mothers. Often the female is superovulated by hormone treatments prior to impregnation to increase the yield of embryos. For example, in cows, superovulation can increase the number of viable embryos recovered from one to about five to fifteen.

With the widespread acceptance and use of artificial insemination for animal breeding, large quantities of sperm are commonly collected and banked for future use, in essence creating a limitless supply of sperm. Equally important, artificial insemination permits the genes from the most desirable animals to be made far more widely available than with natural mating techniques. For example, sperm collected from a single superior bull can be used to impregnate thousands of cows by artificial insemination. Heretofore, however, there has existed no practical method for collecting large numbers of fertilizable ova from females and, as a result, there is no efficient method comparable to artificial insemination for improving the quality of livestock by the widespread breeding of superior females. Embryo transfer which is designed to overcome this problem is inefficient and expensive and therefore not appropriate for widespread use.

The reason large numbers of fertilizable ova have heretofor not been available relates to the reproductive biology of females. Mature males are continuously producing large numbers of sperm. However, in female mammals, only certain cells in the ovaries are capable of maturing into ova. These germ cells, which usually number about 200,000 to 300,000 per ovary in most mammals, are present at birth, are held in the ovary, arrested in an early stage of meiosis and incapable of being fertilized and developing into normal young. Under normal circumstances, a number of these cells begin to develop within the ovary with a periodicity tuned to the animal's sexual cycle. At the appropriate time in the sex cycle, either one or a small number of these cells (depending on whether the animal is a litter bearer) will be released from the ovary, a process known as ovulation. The complex process by which an individual germ cell develops to the point at which ovulation occurs is known as folliculogenesis. Folliculogenesis involves several major steps and the coordinated activities of other cells of the ovary as well as pituitary and ovarian hormones. Following ovulation, the cell or cells (oocytes) released undergo another step in the process of meiosis in which the number of chromosomes in the cells is reduced by half, after which cells become fertilizable ova. This process usually occurs during the movement of the cells from the ovary to the oviduct where fertilization will take place.

To the knowledge and belief of the inventors, there currently exists no known method or process for the development and maturation of large numbers of germ cells into fertilizable ova either in vitro or in vivo. There is a clear need for such a process in order to eliminate the critical limiting factor in all known breeding techniques, the availability of fertilizable ova. Such a process would make possible the use of in vitro fertilization and embryo implantation on a large scale for efficiently reproducing commercially important animals or other important animals (such as endangered species). Perhaps more importantly, it would also make possible the use of these techniques for efficiently improving the quality of herds and of animals by selectively breeding desirable females.

SUMMARY OF THE INVENTION

A method has now been found which allows for the acquisition of greater numbers of fertilizable ova than can be obtained by any other method currently known to the inventors. In the method of this invention, cells obtained from the ovarian tissue of a mammal are incubated in a tissue culture system designed to support the growth and development of the cells into large or reproductively competent oocytes. For the purpose of this invention, "large" or "reproductively competent" oocytes are oocytes which are capable of undergoing a reduction of their chromosome number and thus become fertilizable.

In more detail, the method of this invention comprises:
(a) obtaining cells from the ovarian tissue of a mammal which cells comprise small and medium oocytes;
(b) incubating said cells in a first supplemented tissue culture medium wherein said supplements comprise effective amounts of (i) insulin, (ii) one or more thyroid hormones (iii) one or more neurotransmitters and (iv) one or more purines; followed by
(c) incubating said cells in a second supplemented tissue culture medium wherein said supplements comprise effective amounts of (i) insulin, (ii) one or more thyroid hormones, (iii) one or more gonadotropins and (iv) one or more purines; the effective amounts of said supplements and the time and conditions of said incubations in steps (b) and (c) being sufficient for at least a portion of said small and medium oocytes to grow and develop into reproductively competent oocytes, and
(d) isolating said reproductively competent oocytes from said second tissue culture.

The reproductively competent oocytes may then be induced to undergo a further maturation step involving the reduction of their chromosome number. By this step, the reproductively competent oocytes become ova capable of being fertilized in vitro to form embryos.

DETAILED DESCRIPTION OF THE INVENTION

The cells utilized in the method of this invention are obtained from the ovarian tissue of mammals by retrieving whole ovaries or ovarian fragments at slaughter, surgically or by laparoscopy. The ovaries or ovarian fragments are preferably washed in saline solutions, minced and incubated with proteolytic enzyme preparations. The incubated tissue is then washed several times in balanced saline solution and subjected to mechanical dispersal, e.g. in a trypsinizing vessel, until a suspension of cell masses and individual cells is formed. The cells in the resulting suspensions will comprise large oocytes, small oocytes and medium oocytes and certain support cells such as granulosa and theca cells. Large oocytes, which are also referred to herein as reproductively competent oocytes, are capable of undergoing the step of chromosome reduction which renders them fertilizable. For purposes of this invention, small and medium oocytes are the precursors of large oocytes and are oocytes which are not yet reproductively competent. Small and medium oocytes can be distinguished from large oocytes by size, volume and the absence of an outer cell layer. Methods for preparing the cell suspensions are described in Grob, "Growth and Endocrine Function of Isolated Ovarian Follicles Cultivated in Vivo," *Biology of Reproduction*, 1, 320–323 (1969); Grob, "Enzymatic Dissection of the Mammalian Ovary," *Science*, Oct. 2, 1964, Vol. 146, No. 3640, pages 73–74; Grob, "Monolayer Culture of Ovarian Follicular Elements Derived from Isolated Mouse Follicles," *Biology of Reproduction*, 5, 207–213 (1971).

After the resulting cell suspension is washed, it is resuspended in tissue culture medium. Suitable tissue culture media include commercially available tissue culture media supplemented with effective amounts of insulin, and of one or more thyroid hormones. This tissue culture medium is hereinafter referred to as basic supplemented medium. The basic supplemented medium is also preferably supplemented with effective amounts of one or more glucocorticoids.

The amount of insulin in the basic supplemented medium will generally range from approximately 2.0 to 8.0 μg insulin per ml of media. Suitable thyroid hormones and their suggested quantities in the medium include but are not limited to the preferred hormone, triiodothyronine ($T_3$) (0.1–1.0 μg/ml) and thyroxine ($T_4$) (1.0–10.00 μg/ml). Suitable glucocorticoids for use in this medium, and their suggested quantities in the medium, include but are not limited to the preferred glucocorticoid, cortisone (0.5–2.0 μg/ml), as well as OH-cortisone (1.0–5.0 μg/ml), cortisol (1.0–5.0 μg/ml) and corticosterone (5.0–10.0 μg/ml). Other supplements may be added to the tissue culture medium for optimal results. For example, it is preferable to add approximately 5% to 20% vol/vol fetal bovine serum, approximately 0.5% to 2% vol/vol of an antibiotic such as penicillin, streptomycin and mixtures thereof, and approximately 1% to 2% vol/vol of 200 mM l-glutamine.

Large oocytes present in the ovarian tissue at the time of its removal from the mammal as well as nonviable cells and other nonadherent ovarian cells can be separated from the tissue culture suspension at this point. It has been found that oocytes, upon growing and developing into reproductively competent oocytes, lose their attachment to the remaining cells in the culture vessel. Thus, the reproductively competent oocytes can be recovered en masse, as opposed to individually, by simply removing all liquid medium from the vessel containing the cells, which liquid medium will contain the detached reproductively competent oocytes, and removing said oocytes from said liquid medium, e.g., by aspiration or centrifugation. These recovered oocytes may then be used in the ova maturation step described below.

After removal of the large oocytes, the remaining material in the tissue culture vessel consists of a great number of small and medium size oocytes, follicles and cell masses. These remaining cells are preferably allowed to incubate in the basic supplemented tissue culture medium for several days to ensure their recovery from the stress of the dispersal method and being placed into culture. They may be held in this way for extended periods of time so long as the medium is changed periodically and temperature conditions are maintained. Growth and development of the small and medium oocytes in these cultures is then induced by manipulation of the supplements to the tissue culture medium in a specific manner.

The first step in inducing growth and development of the small and medium oocytes entails transferring them to a specifically-supplemented tissue culture medium. This tissue culture medium comprises the basic supplemented medium described above which is additionally supplemented with effective amounts of one or more neurotransmitters and of one or more purines. This medium is referred to hereinafter as the neurotransmitter-supplemented medium. The preferred neurotransmitter and suggested quantity thereof is norepinephrine (0.01–0.1 μg/ml), but other suitable neurotransmitters include epinephrine (0.1–1.0 μg/ml) and isoproterenol (5.0–10.0 μg/ml). It is believed that the neurotransmitter functions by allowing the cells to develop the membrane receptors necessary for recognizing the pituitary hormones and by inducing cell division of granulosa and theca cells. The purines are any of a number of basic compounds found in living matter having a purine-type molecular structure. The preferred purine and the suggested quantity thereof is hypoxanthine (1–5 mM); however, other purines include adenine, guanine, xanthine, uric acid, caffeine and theobromine.

The neurotransmitter-supplemented medium is preferably further supplemented with fetal bovine serum, an antibiotic and l-glutamine, as discussed above in connection with the basic supplemented medium.

The cells are incubated in the neurotransmitter-supplemented medium under conditions and for a period of time sufficient to allow for development of the membrane receptors mentioned above, generally about twelve to ninety-six hours at a temperature in the range of about 35°C. to 39°C., preferably about 37.5°C.

After this incubation, the cells are transferred to yet another specifically-supplemented tissue culture medium, the basic supplemented medium discussed above additionally supplemented with effective amounts of one or more gonadotropins and of one or more purines. This medium is hereinafter referred to as the gonadotropin-supplemented medium. Examples of such gonadotropins include follicle stimulating hormone, luteinizing hormone and/or human chorionic gonadotropin. The gonadotropins are preferably incorporated in the medium in quantities within the range of about 1 to 100 μg per ml of medium. Suitable purines and quantities thereof are as discussed above in connection with the neurotransmitter-supplemented medium. As with the basic supplemented and neurotransmitter-supplemented media discussed above, the gonadotropin-supplemented medium may be additionally supplemented with fetal bovine serum, antibiotic and/or l-glutamine.

In describing the specially supplemented tissue culture media used in the process of this invention, an attempt has been made to provide specific examples of each type of supplement and suggested quantities of each such specific example to be incorporated into the media. It will be appreciated that the term "effective amount", as it is used to refer to the supplements, is not capable of precise definition as it is impossible to specify with precision the amount of each supplement required. An effective amount of any supplement is intended to be an amount which will enable the small and medium oocytes to grow and develop and mature into reproductively competent oocytes according to this invention.

The cells are incubated in the gonadotropin-supplemented medium under conditions and for a period of time sufficient to allow at least a portion of the small and medium oocytes therein to grow and develop into large or reproductively competent oocytes, generally about ten to seventeen days at a temperature in the range of about 35–39°C., preferably about 37.5°C.

During the incubation periods described above, cohorts of small and medium oocytes grow and become larger. As this occurs, the large oocytes lose their attachment to the cells of the culture vessel as described above. The culture vessels are inspected periodically and detached oocytes are isolated, e.g., by aspiration, for use in the ova maturation step. Each "run" as described above (meaning the incubation of cells, sequentially, in the neurotransmitter-supplemented medium and in the gonadotropin-supplemented medium, followed by recovery of large oocytes) results in the growth and recovery of a significant number of large oocytes. For example, a single run using one cow ovary can result in recovery of between fifty and three hundred large oocytes. A "run" is completed when no more cells grow and develop into large oocytes. After a "run" is completed, the remaining cultures may be incubated in the gonadotropin-supplemented tissue culture medium for a period of about one to four weeks, and then a repeat "run" may be performed. The repeat runs can be performed until the total yield of large oocytes (from a whole ovary) approaches 200,000. Repeat runs are discontinued when two successive runs fail to yield large oocytes. Prior to use in the ova maturation step described below, the large oocytes recovered via the aforementioned method are preferably incubated in the basic gonadotropin-supplemented medium for a period of approximately two days.

A detailed description of the best mode contemplated for carrying out the cell recovery and oocyte growth and development steps described above is as follows:

1. Cell Recovery

Whole ovaries or ovarian fragments are rinsed in Hanks Balanced Salt Solution (HBSS) and sliced or cubed into smaller pieces (50–100 mm in each dimension). These tissue fragments are placed in enzyme preparations (e.g., 0.2% proteolytic enzyme in HBSS) and incubated at 37.5°–39°C. in a shaking water bath until the borders of the fragments appear "feathery" and the fragments tend to stick together when swirled in the incubating flask. The enzyme solution is then decanted and the fragments are washed three times in HBSS without the enzyme content. The fragments are then transferred in HBSS to a trypsinizing flask, placed on a magnetic stirrer and agitated for 10–30 minutes. After stirring, the supernatant fluid which now contains cells and cell aggregates is decanted and collected in sterile centrifuge tubes. The tissue fragments remaining in the trypsinizing flask are resuspended in more HBSS and agitated further until a suspension is formed. This suspension is decanted and pooled with the first suspension. The process is repeated until no coherent tissue fragments remain in the trypsinizing flask. The pooled cell suspensions resulting from these steps are centrifuged at 30–500 x g for 10 minutes. After centrifugation the supernatant fluid is decanted and the cell pellet is retained.

2. Oocyte Growth and Development

The cell pellet is resuspended in tissue culture media. A medium such as Basal Medium, Eagle with Hanks Salts, Minimum Essential Medium with Hanks Salts, Medium 199, Hams F10 Medium and RPMI 1640 Medium, is supplemented with the following additives: 10% fetal bovine serum; 1% antibiotics mixture; 1% 200 mM 1-glutamine; 0.1% $10^{-6}$ M triiodothyronine; 0.1% $10^{-6}$ M Cortisone; and 0.01% insulin. The media thus supplemented are referred to hereinafter as $SM_1$ (basic supplemented media). The cells resulting from the procedure described above and resuspended in $SM_1$ are poured into tissue culture vessels (flasks or petri dishes) and incubated at 37.5°C. for one to two hours.

After this initial period of incubation the cell suspensions are transferred to new culture vessels and fresh $SM_1$ is added to the initial vessel ($V_1$). This results in two types of vessels for incubation, $V_1$ and $V_2$. Both vessel types are returned to the incubator at 37.5°C. $V_1$ cultures contain those cells from the original suspension which had attached to the surface of the vessel. $V_2$ cultures contain those cells which did not attach to the surface of $V_1$. The $V_1$ and $V_2$ cultures are allowed to incubate overnight and the next morning the $V_2$ culture is poured off into another vessel ($V_3$). Fresh $SM_1$ is added to $V_2$, and both $V_1$ and $V_2$ are returned to the incubator. This procedure results in three vessel classes which contain different populations of cell types:

$V_1$ and $V_2$ contain adherent cells of various types including small and medium oocytes, granulosa and theca cells, as well as other structural elements of ovarian architecture, and $V_3$ contains nonadherent ovarian cells of various types including large oocytes and nonviable cells.

The three types of vessels are utilized in different ways:

$V_1$ and $V_2$ are cultured at 37.5°C. with specific media supplements, as described below, to allow growth and development of oocytes therein. $V_3$ is examined under low power microscopy, and the large oocytes are removed by aspiration. These large oocytes are incubated in $SM_3$ (described below) for approximately 48 hours, and are then ready for use in the ova maturation step.

The growing cells in $V_1$ and $V_2$ are allowed to incubate in $SM_1$ for several days to ensure their recovery from the stress of the dispersal method and being placed into culture. Growth and development of the small and medium oocytes in these cultures is induced by manipulation of medium supplements in a specific manner. In all cases, $SM_1$ is utilized as the basic medium, and, from this, two other media are produced:

$SM_2 = SM_1 + 0.5\%$ $10^{-6}$ norepinephrine $+ 0.1\%$ Hypoxanthine (neurotransmitter-modified medium)

$SM_3 = SM_1 + 100$ IU FSH per 100 ml $+ 0.1\%$ Hypoxanthine (gonadotropin-modified medium)

These media are utilized in the following manner:

1. $V_1$ and $V_2$ cultures are incubated in $SM_2$ for 48 hours;

2. Following the 48 hour incubation in SM$_2$ the medium is changed to SM$_3$. The cultures are then maintained at 37.5°C. for 10–17 days. During this period, the cultures are monitored for cell morphology microscopically on a daily basis. The large oocytes grown and developed during this incubation are recovered by aspiration for use in the ova maturation step.

Media is changed every 3–7 days depending upon the acidity of the medium. All media changes are accomplished by pouring off used medium and replacing with fresh SM$_3$.

The next step in the process of this invention is the ova maturation step in which the large oocytes obtained from the aforementioned cell recovery and oocyte growth and development steps are induced to undergo maturation. Maturation is a necessary step prior to fertilization and involves a reduction in the chromosome number in the oocyte. Maturation is carried out by incubating the large oocytes in a tissue culture medium having low nutrients and a high energy source (referred to hereinafter as SM$_4$). Such a medium could comprise, for example, a balanced salt solution such as phosphate buffered saline with sodium lactate, sodium pyruvate and a serum albumin. Examples of commercially available media suitable for use in the maturation step include Wittingham's Medium, Brinster's Medium for Ova Culture, and Dulbecco's PBS with added Bovine Serum Albumin (5%) and Sodium Pyruvate (1%).

To induce maturation, the isolated large oocytes are incubated in the SM$_4$ for a period of time and under conditions suitable to allow the oocytes to undergo chromosome number reduction, generally about 24–48 hours at about 37.5°C. The dishes in which this incubation is performed are preferably monitored microscopically at six hour intervals throughout the incubation period. Formation of the first polar body in a large oocyte is taken as evidence of maturation and fertilizability. At each observation period, mature ova (oocytes containing the first polar body) are isolated from the dish and incubated in fresh samples of SM$_4$. Fifteen to twenty mature ova can be incubated in one small petri dish, to await fertilization by sperm.

The mature ova obtained as described above can be fertilized in vitro by the addition of motile sperm which has incubated in semen extender for one to four hours, after either thawing of a frozen sample or dilution of freshly obtained semen. Large numbers of highly motile sperm are preferably transferred to a dish containing about 15 to 20 mature ova in SM$_4$. Transfer can be accomplished by sterile pipette in low volumes of semen extender (usually less than 0.1 ml). The dishes containing mature ova and sperm are incubated at 37.5°C. for twenty-four hours. Microscopic observation of these dishes is performed at six hour intervals. During the period of incubation, fertilization and early cleavage of the embryos occurs. At each observation period, any embryos seen are removed by micropipette and transferred. The embryos are grown either in microdrops of SM$_4$ suspended in paraffin oil or in individual wells of 96-well tissue culture dishes. These are incubated at 37.5°C. in fresh aliquots of the same fluid in which maturation took place. The embryos usually grow to the blastocyst stage of development in about six to nine days. At this stage of development, the embryos can be utilized in several ways. They may be implanted into the uterus of a surrogate mother for development to parturition (embryo transfer). They may be frozen by controlled freezing in a state of reduced hydration, for storage and subsequent embryo transfer.

The freshly formed or frozen blastocysts produced as described above can be implanted in surrogate uteri using methods known in the art. The transfer is generally accomplished by passage of a catheter containing the blastocyst through the vagina of the surrogate mother (selected at the appropriate stage of the sex cycle) into the uterus. The embryo is then flushed from the catheter into the uterus as close to the functioning corpus luteum as possible.

What is claimed is:

1. A method for obtaining a quantity of reproductively competent oocytes which are capable of undergoing nuclear maturation which comprises:
   (a) obtaining cells from the ovarian tissue of a mammal which cells comprise small and medium oocytes;
   (b) incubating said cells in a first supplemented tissue culture medium wherein said supplements comprise effective amounts of (i) insulin, (ii) one or more thyroid hormones, (iii) one or more neurotransmitters and (iv) one or more purines;
   (c) incubating said cells in a second supplemented tissue culture medium wherein said supplements comprise effective amounts of (i) insulin, (ii) one or more thyroid hormones, (iii) one or more gonadotropins and (iv) one or more purines; the effective amounts of said supplements and the time and conditions of said incubations in steps (b) and (c) taken together being sufficient for at least a portion of said small and medium oocytes to grow and develop into reproductively competent oocytes; and
   (d) isolating said reproductively competent oocytes from said second tissue culture.

2. The method of claim 11 where said first supplemented tissue culture medium is further supplemented with an effective amount of one or more glucocorticoids.

3. The method of claim 1 where said second supplemented tissue culture medium is further supplemented with an effective amount of one or more glucocorticoids.

4. The method of claim 2 where said glucocorticoid is cortisone.

5. The method of claim 3 where said glucocorticoid is cortisone.

6. The method of claim 1 where said thyroid hormone is triiodothyronine.

7. The method of claim 1 where said neurotransmitter is norepinephrine.

8. The method of claim 1 where said purine is hypoxanthine.

9. The method of claim 1 where the cells remaining subsequent to the isolation of said reproductively competent oocytes are retained and are subsequently recycled for use in said method.

10. The method of claim 9 where, prior to recycling said cells, they are allowed to incubate in a tissue culture medium supplemented with insulin, one or more thyroid hormones, one or more gonadotropins, and one or more purines.

11. The method of claim 1 where the cells used in said method are obtained by suspending cells obtained from whole ovaries or ovary fragments in a tissue culture medium.

12. The method of claim 11 where, prior to the use of said cells in said method, reproductively competent oocytes and nonviable cells are isolated from said suspension.

13. The method of claim 1 where said isolated reproductively competent oocytes are subjected to conditions to induce reduction in chromosome number and yield fertilizable ova.

14. The method of claim 12 where said isolated reproductively competent oocytes are subjected to conditions to induce reduction in chromosome number and yield fertilizable ova.

15. The method of claim 13 where said conditions comprise incubation in a low nutrient, high energy source tissue culture.

16. The method of claim 14 where said conditions comprise incubation in a low nutrient, high energy source tissue culture.

17. The method of claim 13 where said fertilizable ova are fertilized by the addition thereto of motile sperm.

18. The method of claim 14 where said fertilizable ova are fertilized by the addition thereto of motile sperm.

19. The method of claim 17 where embryos grown from said fertilized ova are implanted in surrogate uteri.

20. The method of claim 18 where embryos grown from said fertilized ova are implanted in surrogate uteri.

UNITED STATES PATENT AND TRADEMARK OFFICE
CERTIFICATE OF CORRECTION

PATENT NO. : 4,987,080

DATED : January 22, 1991

INVENTOR(S) : Howard S. Grob and Frank Friedman

It is certified that error appears in the above-identified patent and that said Letters Patent is hereby corrected as shown below:

Column 8, line 36: "2. The method of claim 11..." should be
—2. The method of claim 1...—

Signed and Sealed this

Sixteenth Day of June, 1992

Attest:

DOUGLAS B. COMER

*Attesting Officer*     Acting Commissioner of Patents and Trademarks